United States Patent [19]

Bargiotti et al.

[11] Patent Number: 4,684,629

[45] Date of Patent: Aug. 4, 1987

[54] 3'-DEAMINO-3'-HYDROXY-4'-DEOXY-4'-AMINO DOXORUBICIN AND RELATED DAUNORUBICIN

[75] Inventors: Alberto Bargiotti; Michele Caruso; Antonino Suarato; Sergio Penco, all of Milan; Fernando Giuliani, Cassina de'Pecchi, all of Italy

[73] Assignee: Farmitalia Carlo Erba S.p.A., Milan, Italy

[21] Appl. No.: 843,264

[22] Filed: Mar. 24, 1986

[30] Foreign Application Priority Data

Mar. 28, 1985 [GB] United Kingdom ................ 8508079

[51] Int. Cl.[4] ...................... A61K 31/70; C07H 15/24
[52] U.S. Cl. ........................................ 514/34; 536/6.4
[58] Field of Search ............................ 536/6.4; 514/34

[56] References Cited

U.S. PATENT DOCUMENTS 4,366,149  12/1982  Bargiotti et al. ...................... 514/34
4,393,052   7/1983  Bargiotti et al. ...................... 536/6.4

Primary Examiner—Johnnie R. Brown
Assistant Examiner—Elli Peselev
Attorney, Agent, or Firm—Oblon, Fisher, Spivak, McClelland, & Maier

[57] ABSTRACT

Anthracycline glycosides of general formula (I)

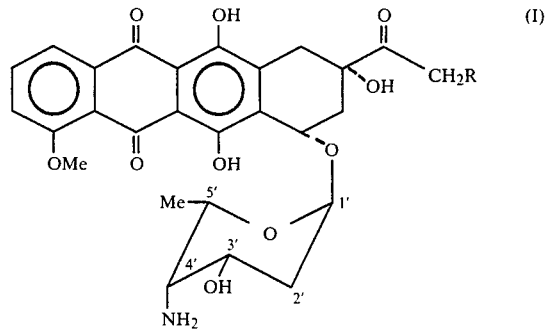

wherein R is hydrogen or hydroxy, and pharmaceutically acceptable salts thereof, are anti-tumor agents.

6 Claims, No Drawings

3'-DEAMINO-3'-HYDROXY-4'-DEOXY-4'-AMINO DOXORUBICIN AND RELATED DAUNORUBICIN

DESCRIPTION

The present invention relates to anthracycline antitumor glycosides, methods for their preparation, compositions containing them and the use of the glycosides.

Daunorubicin (daunomycin) and doxorubicin (adriamycin) are both well-known anthracycline antitumor glycosides, and both their preparation and use are amply described in the prior art. Daunomycinone, the aglycone of daunorubicin, which is one of the starting material used in the preparation of the compounds of the invention is also well-known material and is described and claimed in British Pat. No. 1,003,383.

The present invention provides, in one aspect thereof, a new class of anthracycline glycosides of the formula (I)

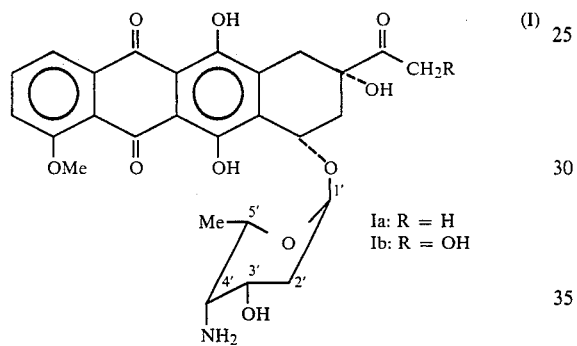

Ia: R = H
Ib: R = OH wherein R is hydrogen or hydroxy, and pharmaceutically acceptable salts thereof such as the hydrochloride. More particularly the new anthracycline glycosides are:
IA: 3'-deamino-3'-hydroxy-4'-deoxy-4'-aminodaunorubicin (R=H)
IB: 3'-deamino-3'-hydroxy-4'-deoxy-4'-aminodoxorubicin (R=OH)

Compounds IA and IB and pharmaceutically acceptable salts thereof are prepared by the following two processes which are also within the scope of the invention. The first process utilizes as its starting material 3'-deamino-4'-deoxy-3',4'-epiiminodaunorubicin (II) whose preparation is illustrated by Scheme I:

SCHEME I

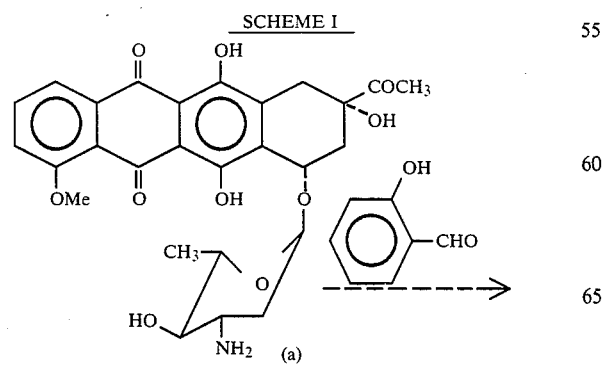

(a)

-continued
SCHEME I

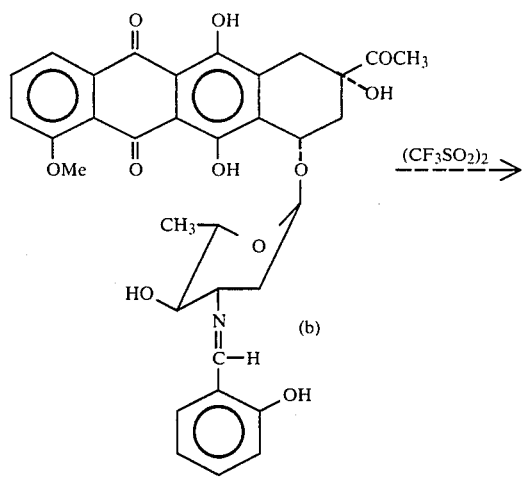

(b)

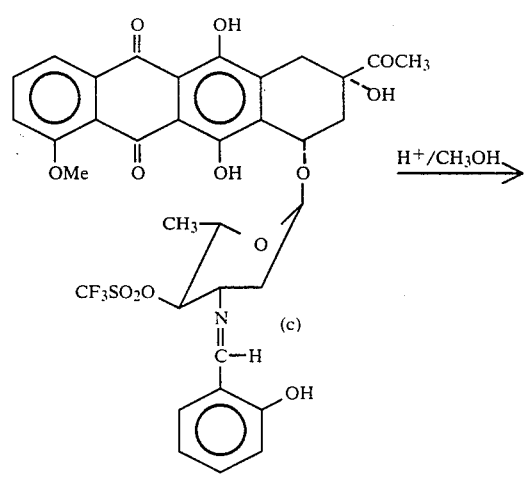

(c)

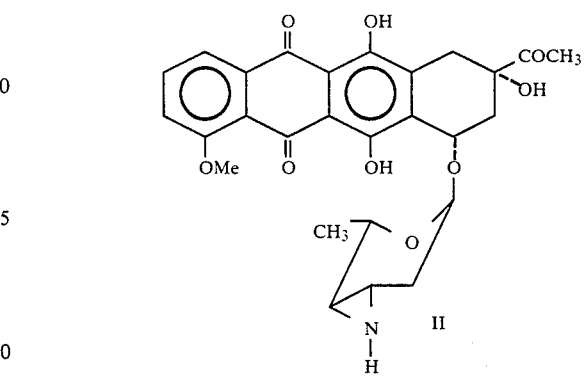

II

The second process involves the use of the novel halosugar 1-chloro-2,4,6-trideoxy-3-O-trifluoroacetyl-4-trifluoroacetamido-L-lyxohexopyranose (III)

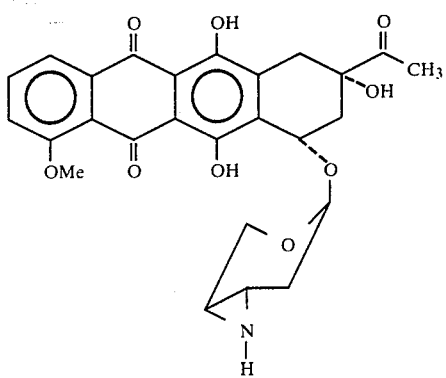

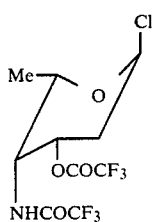

III

The first process according to the invention comprises opening the imino ring of 3'-deamino-4'-deoxy-3',4'-epiimino daunorubicin and trifluoroacetylating the resulting axial 4'-amino group to form a compound of formula (IV):

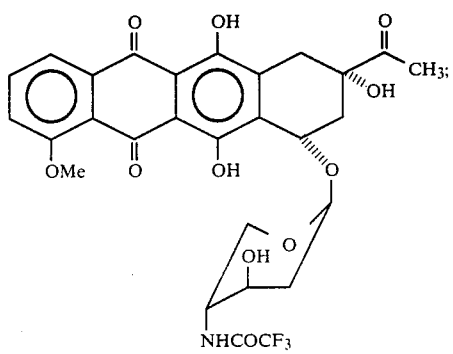

(IV)

converting the compound of formula (IV) into a 3',4'-oxazolidine derivative thereof of formula (V):

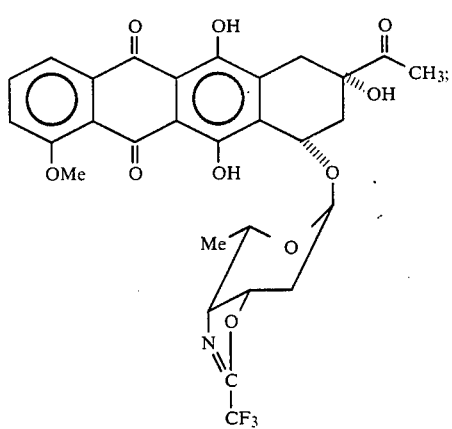

(V)

hydrolysing the compound of formula (V) under acidic conditions to obtain the anthracycline glycoside of formula (I) in which R is hydrogen; if desired, converting the said anthracycline glycoside into a pharmaceutically acceptable salt thereof; if desired, brominating the said anthracycline glycoside of formula (I) or pharmaceutically acceptable salt thereof and hydrolysing the 14-bromo derivative thus obtained to obtain the anthracycline glycoside of formula (I) in which R is hydroxy; and, if desired, converting the anthracycline glycoside of formula (I) in which R is hydroxy into a pharmaceutically acceptable salt thereof.

The preparation of the daunorubicin derivative IA from II by this process is illustrated by the following reaction scheme II:

SCHEME II

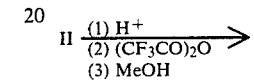

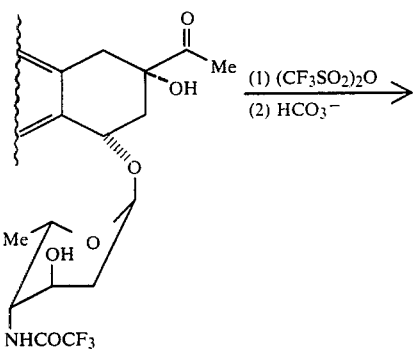

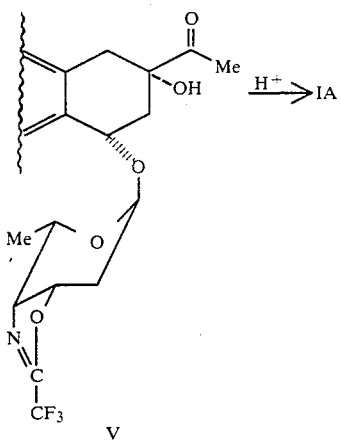

Typically, compound II is dissolved in a mixture of water-acetone and in the presence of p-toluensulfonic acid affords in high yield the trans-diaxial opening product with therefore the L-xylo configuration of the sugar moiety and bearing the amino group at C-4'. The corresponding N-trifluoroacetyl derivative is converted into the 3',4'-oxazolidine derivative V by reacting with triflic anhydride followed by a mild alkaline treatment, from which IA is obtained easily upon acid hydrolysis.

Compound IA is converted to IB by bromination at the 14-position and by hydrolysis of the 14-bromo derivative with aqueous sodium formate. The bromination and hydrolysis conditions are those described in U.S. Pat. No. 3,803,124 or British Pat. No. 1,217,133.

According to an embodiment of the first process, 3'-deamino-4'-deoxy-3',4'-epiimino daunorubicin dissolved in acetone, is treated at room temperature and for 8 hours with p-toluensulfonic acid to afford 3'-deamino-3'-hydroxy-3'-epi-4'-deoxy-4'-amino daunorubicin which is subsequently reacted at room temperature and for 1 hour, in anhydrous methylene dichloride, with trifluoroacetic anhydride to obtain 3'-deamino-3'-hydroxy-3'-epi-4'-deoxy-4'-trifluoroacetamido daunorubicin which is converted, by treatment with trifluoromethansulfonic anhydride at 0° C., in anhydrous methylene dichloride and in the presence of dry pyridine, into its 3'-O-trifluoromethanesulfonate derivative which after a mild alkaline treatment with 5% aqueous sodium bicarbonate, gives its 3',4'-oxazolidine derivative, from which upon acid hydrolysis with 0.5N hydrochloric acid, in methanolic solution at room temperature and for 1 hour, the desired 3'-deamino-3'-hydroxy-4'-deoxy-4'-amino daunorubicin (R=H) is isolated as its hydrochloride and, if desired, is reacted with bromine in chloroform to obtain its 14-bromo derivative from which, after a mild hydrolysis at room temperature and for 48 hours under nitrogen with an aqueous solution of sodium formate, the compound of formula (I) (R=OH) is obtained as a free base and, by treatment with anhydrous methanolic hydrogen chloride, is isolated as its hydrochloride.

The second process of the invention comprises condensing daunomycinone with a compound of formula (III):

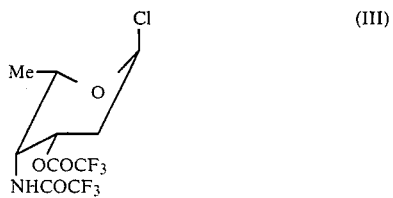

followed by treatment with a mild alkali to obtain a compound of formula (VII):

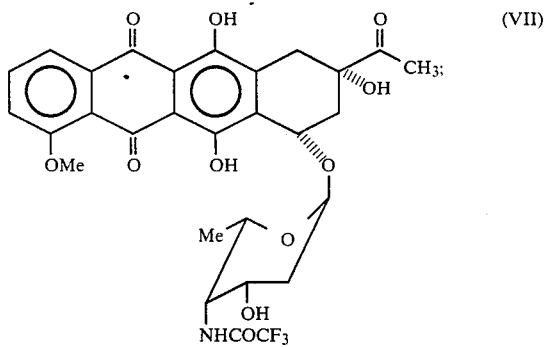

removing the N-trifluoroacetyl group from the compound of formula (VII) to obtain the anthracycline glycoside of formula (I) in which R is hydrogen; if desired, converting the said anthracycline glycoside into a pharmaceutically acceptable salt thereof; if desired, brominating the said anthracycline glycoside of formula (I) or pharmaceutically acceptable salt thereof and hydrolysing the 14-bromo derivative thus obtained to obtain the anthracycline glycoside of formula (I) in which R is hydroxy; and, if desired, converting the anthracycline glycoside of formula (I) in which R is hydroxy into a pharmaceutically acceptable salt thereof.

The preparation of the daunorubicin derivative IA by this alternative process is illustrated by the following reaction scheme III:

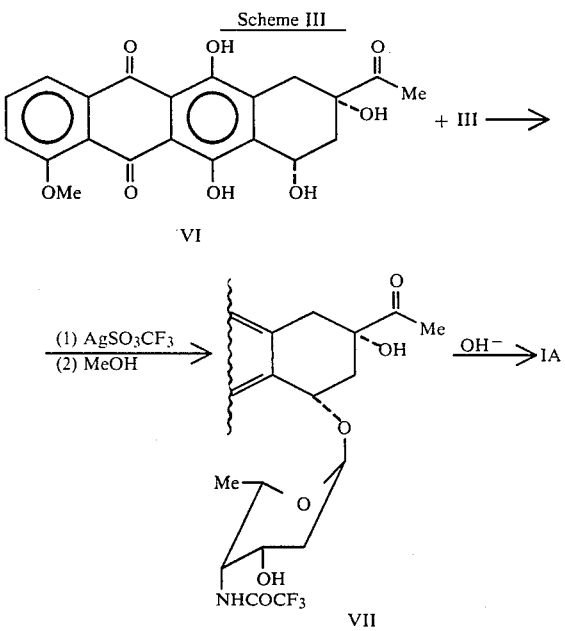

In scheme III, daunomycinone (VI) is condensed with III in the presence of silver trifluoromethansulphonate to form the protected glycoside VII from which IA is obtained by removing the N-trifluoroacetyl protecting group by mild alkaline hydrolysis. The conditions under which the condensation is carried out may be those described in U.S. Pat. No. 4,112,074.

Again, IA can be converted to IB by bromination at the 14-position and by hydrolysis of the 14-bromo derivative with aqueous sodium formate. The bromination and hydrolysis conditions are those described in U.S. Pat. No. 3,803,124 or British Pat. No. 1,217,133.

According to an embodiment of the second process daunomycinone, dissolved in dry methylene dichloride, is reacted at room temperature and for 1 hour with 1-chloro-2,4,6,-trideoxy-3-O-trifluoroacetyl-4-trifluoroacetamido-L-lyxohexopyranosyl-chloride in the presence of molecular sieves and silver trifluoromethanesulphonate to obtain a N,O-protected glycoside which, after treatment with an aqueous NaHCO$_3$ saturated solution, gives 3'-deamino-3'-hydroxy-4'-deoxy-4'-trifluoroacetamido daunorubicin which, dissolved in acetone, is submitted at a temperature of 0° C. and for 1 hour, to a mild alkaline hydrolysis with 0.1N aqueous sodium hydroxide to give the compound of formula (I) (R=H) as a free base which, by treatment with anhydrous methanolic hydrogen chloride is isolated as its hydrochloride and, if desired, is reacted with bromine in chloroform to obtain its 14-bromo derivative from which, after hydrolysis at room temperature and for 48 hours under nitrogen with an aqueous solution of sodium formate, the compound of formula (I) (R=OH) is obtained as a free base and by treatment with anhydrous methanolic hydrogen chloride, is isolated as its hydrochloride.

The present invention also provides a pharmaceutical composition comprising as active ingredient an anthracycline glycoside of formula (I) or a pharmaceutically acceptable salt thereof together with a pharmaceutically acceptable carrier or diluent. A therapeutically effective amount of a compound of the invention is combined with an inert carrier. Conventional carriers may be used and the compositions may be formulated in conventional manner. The compounds of the invention are useful in methods of treatment of the human or animal body by therapy. In particular the compounds of the invention are useful as antitumor agents by administering a therapeutically effective amount of the compound to a patient.

The following Examples illustrate the invention.

EXAMPLE 1

Preparation of 2,4,6-trideoxy-3-O-trifluoroacetyl-4-trifluoroacetamido-L-lyxo-hexopyranosyl-chloride (III)

To a solution of 0.49 g of 2,4,6-trideoxy-4-trifluoroacetamido-L-lyxohexopyranose in 30 ml of anhydrous methylene dichloride was added 5 ml of trifluoroacetic anhydride at 0° C. After two hrs at 0° C. and one hr at room temperature, the reaction mixture was evaporated to give the corresponding 1,3-O-ditrifluoroacetate as a syrup, which was directly dissolved in 20 ml of anhydrous diethyl ether and saturated at 0° C. with dry hydrogen chloride.

After standing at 0° C. overnight, the reaction mixture was evaporated in vacuum to give the title compound (III) suitable for the subsequent coupling reaction without further purification.

EXAMPLE 2

Preparation of 3'-deamino-3'-hydroxy-4'-deoxy-4'-aminodaunorubicin (IA, R=H)

The coupling of 0.9 g of daunomycinone, in 120 ml of dry methylene dichloride with 0.7 g of III, in the presence of molecular sieves (4 Å, Merck), was performed using 0.580 silver trifluoromethanesulphonate, in 20 ml of diethyl ether, as catalyst. After one hr under vigorous stirring at room temperature, the reaction mixture was treated with saturated aqueous sodium hydrogen carbonate, and the organic phase was then separated off and evaporated under vacuum.

Chromatographic purification of the crude residue on a silica gel column using a 98:2 by volume methylene dichloride:methanol, gave 0.810 g of 3'-desamino-3'-hydroxy-4'-deoxy-4'-trifluoroacetamido daunorubicin; m.p. 146°–147° C. (with decomposition). FD-MS 623 [M]$^\pm$, TLC on plates (Merck Kieselgel F 254) using the solvent system: methylene dichloride:methanol (10:1 by volume) Rf=0.31.

NMR (200 MHz, CDCl$_3$) inter alia δ 13.97 (s, 1H, OH-6); 13.45 (s, 1H—OH-11), 8.03 (d, J=8.0 Hz, 1H, H1), 7.79 (t, J=8.0 Hz, 1H, H2), 7.39 (d, J=8.0 Hz, 1H, H3), 6.52 (d, J=9.2 Hz, 1H, NH), 5.53 (bd, J=4.3 Hz, 1H, H1'), 5.21 (dd, J=4.2, 2.3 Hz, 1H, H7), 4.36 (s, 1H, OH-9), 4.32 (bq, J=6.7 Hz, 1H, H5'), 4.3–4.2 (m, 2H, H3' and H4'), 4.05 (s, 3H, OCH$_3$), 3.18 (dd, J=18.8, 1.1 Hz, 1H, H10$_{eq}$), 2.88 (d, J=18.8 Hz, 1H, H10$_{ax}$), 2.40 (s, 3H, COCH$_3$), 2.24 (ddd, J=15.0, 2.3, 1.1 Hz, 1H, H8$_{eq}$), 2.12 (dd, J=15.0, 4.2 Hz, 1H, H8$_{ax}$), 2.00 (bd, J=13.0, 4.8 Hz, 1H, H2'$_{eq}$), 1.67 (ddd, J=13.0, 12.0, 4.3 Hz, 1H, H2'$_{ax}$), 1.23 (d, J=6.7 Hz, 3H, $\underline{CH_3}$—CH). 0.65 g of the N-trifluoroacetyl derivative was dissolved in 10 ml of acetone and treated at 0° C. with 50 ml of 0.1N aqueous sodium hydroxide. After 1 hr the solution was adjusted to pH 8.1 and extracted repeatedly with methylene dichloride. The combined organic extracts, after being dried and concentrated to a small volume were acidified to pH 3.5 with anhydrous methanolic hydrogen chloride. Upon addition of an excess of diethyl ether there was obtained 0.550 g of 3'-deamino-3'-hydroxy-4'-deoxy-4'-amino-daunorubicin (IA) as the hydrochloride. m.p. 145°–146° C. (with decomposition) Rf=0.35. TLC system CH$_2$Cl$_2$/MeOH/H$_2$O (150:42:6 by volume).

EXAMPLE 3

3'-deamino-3'-hydroxy-4'-deoxy-4'-aminodoxorubicin (IB, R=OH)

0.2 g of 3'-deamino-3'-hydroxy-4'-deoxy-4'-amino daunorubicin in dry methanol (4,5 ml) and dioxane (7,5 ml) is treated with ethyl orthoformate (0.2 ml) and 0.75 ml of a solution of bromine in dry methylene chloride (9.5 g in 100 ml).

After 3 hours at 12°–15° C., the reaction mixture is poured into a mixture of diethylether (40 ml) and petroleum ether (20 ml).

The resulting precipitate, after filtration and washing with diethyl ether, is dissolved in 4 ml of acetone and treated with 0.25N aqueous hydrogen bromide (4 ml).

After 15 hours at room temperature sodium formate (0.3 g) in water (4.5 ml) was added and the reaction mixture was stirred under nitrogen for two days and them evaporated to dryness.

The residue is dissolved in 80 ml of 2:1 methylene chloride-methanol and washed with 2.5% aqueous sodium hydrogen carbonate (35 ml).

The aqueous phase is extracted with methylene chloride until the extracts are no longer coloured, them the organic phase is combined with the methylene chloride extracts, dried on anhydrous sodium sulphate and evaporated to a small volume (15 ml) under vacuum.

The red solution, adjusted to pH 3.5 (Congo red) with anhydrous methanolic hydrogen chloride is mixed with diethyl ether in excess to give 3' deamino-3'-hydroxy-4'-deoxy-4'-amino-doxorubicin as the hydrochloride (0.165 g) m.p. 149°–150° C. Rf=0.16.

TLC system CH$_2$Cl$_2$/MeOH/H$_2$O (150:42:6 by volume).

EXAMPLE 4

Preparation of
3'-deamino-4'-deoxy-3',4'-epiimino-daunorubicin (II)

Scheme I. A solution of 2 g of 4'-epidaunorubicin (a) in a mixture of 80 ml of water and 20 ml of acetone, was treated at room temperature with 0.5 ml of salicylaldehyde at pH 8.

After 10 min. ethyl acetate was added and the organic phase separated off, washed with water twice, dried over anhydrous sodium sulphate, filtered and evaporated to dryness under vacuum.

The residue was first triturated with hexane to eliminate the traces of salicylaldehyde, then crystallized from dichloromethane-hexane to give 4-epi-N-salicylidene-daunorubicin (b) m.p. 125° C. dec. Rf 0.45 on TLC Kieselgel F 254 (Merck) using as eluent the solvent mixture $CH_2Cl_2$-Acetone (8/2 v/v).

To a solution of 2 g of 4'-epi-N-salicylidene daunorubicin (b) in 20 ml of anhydrous dichloromethane and 2 ml of dry pyridine kept at −10° C., was added a solution of 0.8 ml of triflic anhydride.

After 1 hr at −10° C., the mixture was diluted with dichloromethane and washed with water, cold 0.1M HCl, cold aqueous 5% $NaHCO_3$ and water.

The organic phase, dried over anhydrous sodium sulphate, was filtered off and the solvent removed in vacuo to give (c).

Rf 0.75 on TLC Kieselgel F 254 (Merck) using as eluent the solvent mixture $CH_2Cl_2$-acetone (95:5 v/v).

The crude product (c) was dissolved in 50 ml of methanol and added with 0.2 g of p-toluenesulfonic acid monohydrate.

The solution was kept at room temperature for 1 hr, then was added 100 ml of water and extracted with little dichloromethane. The aqueous phase was adjusted to pH 8 with 0.1M NaOH and dichloromethane added.

The organic phase was separated off, washed with water, dried over anhydrous sodium sulphate and the solvent evaporated in vacuum to small volume.

The mixture was purified by chromatography on a column of silica gel buffered at pH 7 using dichloromethane-ethanol as eluent.

The eluate containing the product (II) (m.p. 203°-205° C.) was washed with water, evaporated in vacuum, picked up with a little dichloromethane and added with 2 ml of cold acetic acid followed by hexane. The precipitate was collected on a sintered glass, washed with hexane-diethyl ether and dried in vacuum.
m.p. 218° C. dec.
FD MS 509 [M+]
Rf 0.38 on TLC Kieselgel F 254 (Merck) using as eluent the mixture $CH_2Cl_2$—$CH_3OH$—$CH_3COOH$—$H_2O$ (30:4:1:0.5, v/v).
NMR (200, MHz, $CDCl_3$): 13.97 (s, 1H, $\underline{OH}$6); 13.29 (s, 1H, $\underline{OH}$11); 5.31 (dd, J=2.3, 6 Hz, 1H, $\underline{H1'}$); 5.25 (dd, J=2.2, 4 Hz, 1H, $\underline{H7}$); 4.41 (qd, J=1.3, 6.5 Hz, 1H, $\underline{H5'}$); 4.08 (s, 3H, $\underline{OCH}_3$); 2.1–2.3 (m, 3H, $\underline{H4'}$, $\underline{H3'}$, $\underline{H2'\ ax}$); 1.84 (ddd, J=2.3, 5.4, 15.5 Hz, 1H, $\underline{H2'\ eq}$); 1.35 (d, J=6.5 Hz, 3H, $\underline{CH}_3$).

EXAMPLE 5

3'-Deamino-3'-hydroxy-3'-epi-4'-deoxy-4'-trifluoroacetamide daunorubicin (IV)

To a solution of 3 g of 3'-deamino-4'-deoxy-3',4'-epiimino daunorubicin (II) in 200 ml of acetone, was added 0.5 g of p-toluenesulfonic acid monohydrate. The mixture was kept at room temperature for 8 hrs, then was added water and methylene dichloride. The aqueous phase was adjusted to pH 8 with 0.1N aqueous sodium hydroxyde. The organic phase was separated off, washed with water, dried over anhydrous sodium sulphate and the solvent evaporated in vacuum to small volume. The crude glycoside was purified by chromatography on a column of silica gel using methylene dichloride-methanol-water (100:10:0.5 by volume) as eluent. The product (2.5 g) was isolated as the hydrochloride; m.p. 80° C. dec., FD-MS 527 [M]±, TLC on Kieselgel plates (Merck F 254) using solvent system: methylene dichloride:methanol:acetic acid:water (30:4:1:0.5 by volume) Rf 0.20. NMR (200 MHz, $CDCl_3$) inter alia 8.01 (dd, J=8.0, 1.0 Hz, 1H, H−1); 7.76 (t, J=8.0, 1H, H−2); 7.36 (dd, J=8.0, 1.0 Hz, 1H, H−3); 5.42 (bd, J=3.7 Hz, 1H, H1'); 5.19 (dd, J=4.0, 2.1 Hz, 1H, H7); 4.55 (dq, J=6.6, 1.9 Hz, 1H, H−5'); 4.06 (s, 3H, $OCH_3$); 3.84 (ddd, J=4.0, 3.5, 3.0 Hz, 1H, H3'); 3.12 (dd, J=18.9, 1.5 Hz, 1H, $H10_{eq}$); 2.98 (d, J=18.9 Hz, 1H, $H10_{ax}$); 2.68 (m, 1H, H4'); 2.40 (s, 3H, $COCH_3$); 2.34 (ddd, J=15.0, 2.1, 1.5 Hz, 1H, $H8_{eq}$); 2.9 (dd, J=15.0, 4.0 Hz, 3.7 Hz, 1H, $H2'_{ax}$); 1.71 (bdd, J=15.2, 3.0 Hz, 1H, $H2'_{eq}$); 1.22 (d, J=6.6 Hz, 3H, $CH_3$—CH).

Then the N-trifluoroacetylderivative (IV) was obtained as follows: 2.0 g of the hydrochloride was suspended in 100 ml anhydrous methylene dichloride and treated with 2 ml of trifluoroacetic anhydride under stirring. After 1 hour to the mixture were added 50 ml of methanol and aqueous satured sodium bicarbonate. The organic phase was separated off, washed with water, dried over anhydrous sodium sulphate, filtered off and the solvent removed in vacuum to give IV (2 g). m.p. 170° C.; FD-MS 623 [M]±; TLC on Kieselgel plates (Merck F 254) using solvent system: methylene dichloride:acetone (4:1 by volume) Rf 0.30.

EXAMPLE 6

Preparation of the 3',4'-oxazolidine derivative V 2 g of IV in 50 ml of anhydrous methylene dichloride and 2 ml of dry pyridine was converted in its 3'-O-trifluoromethanesulfonate derivative by treatment with 0.8 ml of trifluoromethanesulfonic anhydride at 0° C. The mixture was diluted with methylene dichloride and washed with water, cold 0.1 hydrochloric acid, cold aqueous 5% sodium bicarbonate and water.

The organic phase, dried over anhydrous sodium sulphate, was filtered off and kept at 30° C. After half hour the solvent was removed in vacuum to give the 3',4'-oxazolidine derivative V (1.5 g). TLC on Kieselgel plates (Merck F 254) using as eluent the solvent system: methylene dichloride:acetone (95:5 by volume) Rf 0.30; FD-MS 605 [M]±

NMR (200 MHz, CDCl₃) inter alia 5.48 (dd, J=8.0, 6.0 Hz, 1H, H—1'); 5.05 (dt, J=9.9, 3.0 Hz, 1H, H3'); 4.26-4.21 (m, 1H, H4'); 4.20-4.10 (m, 1H, H5'); 4.06 (s, 3H, OCH₃), 2.60 (ddd, J=15.9, 6.0, 3.0 Hz, 1H, H2'$_{eq}$); 2.40 (s, 3H, COCH₃); 1.75 (ddd, J=15.9, 8.0, 3.0 Hz, 1H, H2'$_{ax}$).

EXAMPLE 7

Preparation of IA (R=H)

2 g of product V was dissolved in 50 ml of methanol and added with 1 ml of aqueous 0.5N hydrochloric acid. The solution was kept at room temperature for 1 hr, then was added water and extracted with methylene dichloride in order to eliminate by-products. The aqueous phase was adjusted to pH 8 with 0.1N aqueous sodium hydroxide and methylene dichloride added. The organic phase was separated off, washed with water, dried over anhydrous sodium sulphate and the solvent evaporated in vacuum. To the residue dissolved in methylene dichloride anhydrous methanolic hydrogen chloride and diethyl ether were added to give IA as hydrochloride.

Biological activity of compounds Ia, Ib.

The compounds have been tested "in vitro" and "in vivo" in order to ascertain their cytotoxicity and antitumor activity in experimental animals. The colony inhibition test against HeLa cells (treatment for 24 hrs) showed that compound Ia is cytotoxic (ID$_{50}$=7 ng/ml) as daunorubicin (ID$_{50}$=9 ng/ml).

The primary screening "in vivo" was carried out in CDF-1 mice bearing P 388 ascitic leukemia (10⁶ cells/mouse). Results are reported in Table I. The compounds Ia, Ib are more active than the parent drugs.

TABLE 1

Antitumor activity against P₃₈₈ leukemia, treatment ip on day 1

| Compound | Dose (ng/kg) | T/C %[a] | Toxic deaths[b] |
|---|---|---|---|
| Daunorubicin | 2.9 | 170 | 0/10 |
| | 4.4 | 170 | 0/10 |
| | 6.6 | 170 | 3/10 |
| Ia | 10.0 | 165 | 0/10 |
| | 15.0 | 180 | 0/10 |
| | 22.5 | 200 | 0/10 |
| Doxorubicin | 10.0 | 225 | 0/10 |
| Ib | 4.4 | 220 | 0/10 |
| | 6.6 | 230 | 0/10 |
| | 10.0 | 310 | 0/10 |

TABLE 1-continued

Antitumor activity against P₃₈₈ leukemia, treatment ip on day 1

| Compound | Dose (ng/kg) | T/C %[a] | Toxic deaths[b] |
|---|---|---|---|
| | 15.0 | 215 | 3/10 |

[a]Median survival time: % over untreated controls
[b]Evaluated on the basis of autoptic findings on dead mice.

The compound IB has been tested in comparison with Doxorubicin against advanced mammary carcinoma spontaneously arising in C3H/He mice. The compounds were administered iv once a week for four weeks. The results are reported in Table 2. The activity at the optimal dose was the same for both compounds (6 mg/kg of Doxorubicin; 5.3 mg/kg of IB). However, the cardiotoxicity of IB was drastically reduced in comparison with Doxorubicin. In fact, all the animals treated with Doxorubicin showed cardiac lesions both at atrial and ventricular level and the severity of the lesions was high; on the contrary animals treated with IB showed a lower severity and a lower percent of affected mice in comparison with the parent drug.

TABLE 2

Activity, toxicity and cardiotoxicity of IB against advanced mammary carcinoma[1]

| | | | | | Cardiotoxicity[6] | | | |
|---|---|---|---|---|---|---|---|---|
| | | | | | Atrium | | Ventricle | |
| Compound | mg/kg[2] | Tumor growth[3] | T/C %[4] | Toxic[5] Deaths | affected mice(%) | grade | affected mice(%) | grade |
| Doxorubicin | 6 | 65 | 138 | 0/5 | 100 | 1.6 | 100 | 1.2 |
| | 7.5 | 84 | 125 | 5/5 | 100 | 3.2 | 100 | 3.6 |
| IB | 2.7 | 32 | 98 | 0/5 | 25 | 0.1 | 0 | 0 |
| | 3.8 | 34 | 129 | 0/5 | 20 | 0.1 | 60 | 0.3 |
| | 5.3 | 59 | 148 | 1/5 | 40 | 0.2 | 80 | 0.4 |

[1]Experiment was performed in C3H/He mice inoculated s.c. with 20 × 10⁶ mammary carcinoma cells.
[2]Treatment iv started when tumor was palpable (once week for four weeks).
[3]Evaluated once week after last treatment.
[4] $\frac{\text{Median survival time of treated mice}}{\text{Median survival time of controls}} \times 100$
[5]Evaluated on the basis of autoptic findings
[6]Evaluated on semithin section of miocardial tissue (by light microscopy)

We claim:

1. An anthracycline glycoside of the general formula (I):

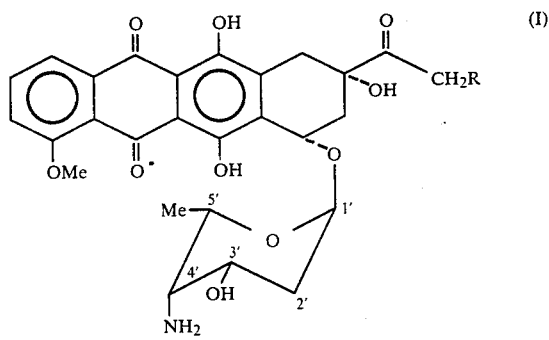

wherein R is hydrogen or hydroxy, and pharmaceutically acceptable salts thereof.

2. A compound according to claim 1, which is 3'-deamino-3'-hydroxy-4'-deoxy-4'-aminodaunorubicin or its hydrochloride.

3. A compound according to claim 1, which is 3'-deamino-3'-hydroxy-4'-deoxy-4'-aminodoxorubicin or its hydrochloride.

4. A process for the preparation of the compound of claim 1, in which 3'-deamino-4'-deoxy-3',4'-epiimino daunorubicin dissolved in acetone, is treated at room temperature and for 8 hours with p-toluensulfonic acid to afford 3'-deamino-3'-hydroxy-3'-epi-4'-deoxy-4'-amino daunorubicin which is subsequently reacted at room temperature and for 1 hour, in anhydrous methylene dichloride, with trifluoroacetic anhydride to obtain 3'-deamino-3'-hydroxy-3'-epi-4'-deoxy-4'-trifluoroacetamido daunorubicin which is converted, by treatment with trifluoromethanesulfonic anhydride at 0° C., in anhydrous methylene dichloride and in the presence of dry pyridine, into its 3'-O-trifluoromethanesulfonate derivative which after a mild alkaline treatment with 5% aqueous sodium bicarbonate, gives its 3',4'-oxazolidine derivative, from which upon acid hydrolysis with 0.5N hydrochloric acid, in methanolic solution at room temperature and for 1 hour, the desired 3'-deamino-3'-hydroxy-4'-deoxy-4'-amino daunorubicin (R=H) is isolated as its hydrochloride and, thereafter reacted with bromine in chloroform to obtain its 14-bromo derivative from which, after a mild hydrolysis at room temperature and for 48 hours under nitrogen with an aqueous solution of sodium formate, the compound of formula (I) (R=OH) is obtained as a free base and, by treatment with anhydrous methanolic hydrogen chloride, is isolated as its hydrochloride.

5. A pharmaceutical composition having antitumor activity against P388 leukemia tumors, comprising a therapeutically effective amount of the compound of claim 1 and inert carrier therefor.

6. A method of inhibiting the growth of P388 leukemia tumors comprising administering, to a mammal, afflicted with said tumor a therapeutically effective amount of the compound of claim 1.

* * * * *